US008415306B2

(12) United States Patent
Diem et al.

(10) Patent No.: US 8,415,306 B2
(45) Date of Patent: Apr. 9, 2013

(54) INSULIN-LIKE GROWTH FACTOR 1 RECEPTOR BINDING PEPTIDES (75) Inventors: Michael Diem, Radnor, PA (US); Karyn O'Neil, Radnor, PA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 13/115,523

(22) Filed: May 25, 2011

(65) Prior Publication Data

US 2011/0294748 A1 Dec. 1, 2011

Related U.S. Application Data (60) Provisional application No. 61/348,937, filed on May 27, 2010.

(51) Int. Cl.
*A61K 39/395* (2006.01)
*A61K 38/10* (2006.01)
*C12P 21/04* (2006.01)
*C12P 21/08* (2006.01)
*C12N 15/00* (2006.01)
*C12N 5/00* (2006.01)
*C07H 21/04* (2006.01)

(52) U.S. Cl. ............ 514/21.4; 424/134.1; 424/178.1; 435/69.7; 435/320.1; 435/325; 530/326; 530/327; 530/387.3; 514/21.5; 536/23.1; 536/23.4

(58) Field of Classification Search .................. None
See application file for complete search history.

(56) References Cited

U.S. PATENT DOCUMENTS

| 4,816,567 | A | 3/1989 | Cabilly et al. |
| 6,329,508 | B1 | 12/2001 | Friden |
| 7,388,079 | B2 | 6/2008 | Pardridge et al. |
| 2002/0009491 | A1 | 1/2002 | Rothbard et al. |
| 2002/0013266 | A1 | 1/2002 | Bentley et al. |
| 2004/0034888 | A1 | 2/2004 | Liu et al. |
| 2004/0086942 | A1 | 5/2004 | Lowman et al. |
| 2004/0214272 | A1 | 10/2004 | La Rosa et al. |
| 2005/0085419 | A1 | 4/2005 | Morrison et al. |
| 2006/0051317 | A1 | 3/2006 | Batrakova et al. |
| 2007/0081992 | A1 | 4/2007 | Pardridge et al. |
| 2007/0083334 | A1 | 4/2007 | Mintz et al. |
| 2009/0130105 | A1 | 5/2009 | Glaser et al. |
| 2010/0021477 | A1 | 1/2010 | Tsui et al. |
| 2010/0028370 | A1 | 2/2010 | Zankel et al. |

OTHER PUBLICATIONS

Fishwild, et al., "High-avidity human IgGκ monoclonal antibodies from a novel strain of minilocus transgenic mice," Nature Biotechnology, 14: 845-851 (1996).
Gentz, et al., "Bioassay for trans-activation using purified human immunodeficiency virus *tat*-encoded protein: Trans-activation requires mRNA synthesis," Proceedings of the National Academy of Science USA, 86: 821-824 (1989).
Knappik, et al., "Fully Synthetic Human Combinatorial Antibody Libraries (HuCAL) Based on Modular Consensus Frameworks and CDRs Randomized with Trinucleotides," Journal of Molecular Biology, 296: 57-86 (2000).
Kohler, et al., "Continuous cultures of fused cells secreting antibody of predefined specificity," Nature, 256: 495-497 (1975).
Krebs, et al., High-throughput generation and engineering of recombinant human antibodies, Journal of Immunological Methods, 254: 67-84 (2001).
Lonberg, et al., "Antigen-specific human antibodies from mice comprising four distinct genetic modifications," Nature, 368: 856-859 (1994).
Mendez, et al., "Functional transplant of megabase human immunoglobulin loci recapitulates human antibody response in mice," Nature Genetics, 15: 146-156 (1997).
Perrière, et al., "A functional in vitro model of rat blood-brain barrier for molecular analysis of efflux transporters," Brain Research, 1150: 1-13 (2007).
Perrière, et al., "Puromycin-based purification of rat brain capillary endothelial cell cultures. Effect on the expression of blood-brain barrier-specific properties," Journal of Neurochemistry, 93: 279-289 (2005).
Queen, et al., "A humanized antibody that binds to the interleukin 2 receptor," Proceedings of the National Academy of Science USA, 86: 10029-10033 (1989).
Wilson, et al., "The Structure of an Antigenic Determinant in a Protein," Cell, 37: 767-778 (1984).
Yu, et al., "Reciprocal Interactions of Insulin and Insulin-Like Growth Factor I in Receptor-Mediated Transport across the Blood-Brain Barrier," Endocrinology, 147(6): 2611-2615 (2006).
Zhang, et al., "Conjugation of brain-derived neurotrophic factor to a blood-brain barrier drug targeting system enables neuroprotection in regional brain ischemia following intravenous injection of the neurotrophin," Brain Research, 889: 49-56 (2001).

*Primary Examiner* — Marianne P Allen
(74) *Attorney, Agent, or Firm* — Kirk Baumeister (57) ABSTRACT

The present invention relates to insulin-like growth factor 1 receptor binding peptides, polynucleotides encoding them, and methods of making and using the foregoing.

12 Claims, 2 Drawing Sheets

IGF-1R Binding Peptide-AP

SEQUENCE LISTING

<160> NUMBER OF SEQ ID NOS: 31

<210> SEQ ID NO 1
<211> LENGTH: 14
<212> TYPE: PRT
<213> ORGANISM: Artificial Sequence
<220> FEATURE:
<223> OTHER INFORMATION: IGF1R binding peptide from pIX library

<400> SEQUENCE: 1

Thr Gly Cys Asp Phe Pro Glu Leu Cys Arg Gly Cys His Pro
1               5                   10

<210> SEQ ID NO 2
<211> LENGTH: 15

```
<212> TYPE: PRT
<213> ORGANISM: Artificial Sequence
<220> FEATURE:
<223> OTHER INFORMATION: IGF1R binding peptide from pIX library

<400> SEQUENCE: 2

Ala Glu Cys Glu Trp Pro Trp Leu Thr Leu Glu Leu Cys Gln Ser
 1               5                  10                  15

<210> SEQ ID NO 3
<211> LENGTH: 15
<212> TYPE: PRT
<213> ORGANISM: Artificial Sequence
<220> FEATURE:
<223> OTHER INFORMATION: IGF1R binding peptide from pIX library

<400> SEQUENCE: 3

Pro Phe Cys Tyr Ser Gly Gly Pro Leu Pro Tyr Pro Cys Thr Tyr
 1               5                  10                  15

<210> SEQ ID NO 4
<211> LENGTH: 15
<212> TYPE: PRT
<213> ORGANISM: Artificial Sequence
<220> FEATURE:
<223> OTHER INFORMATION: IGF1R binding peptide from pIX library

<400> SEQUENCE: 4

Pro Val Cys Pro Ser Phe Cys Tyr Asp Gln Tyr Val Cys Pro Thr
 1               5                  10                  15

<210> SEQ ID NO 5
<211> LENGTH: 15
<212> TYPE: PRT
<213> ORGANISM: Artificial Sequence
<220> FEATURE:
<223> OTHER INFORMATION: IGF1R binding peptide from pIX library

<400> SEQUENCE: 5

Phe Thr Cys Ala Val Tyr Ser Leu Ser Glu Leu Asp Cys Arg Asp
 1               5                  10                  15

<210> SEQ ID NO 6
<211> LENGTH: 15
<212> TYPE: PRT
<213> ORGANISM: Artificial Sequence
<220> FEATURE:
<223> OTHER INFORMATION: IGF1R binding peptide from pIX library

<400> SEQUENCE: 6

Leu Ser Cys Tyr Asp Pro Thr Leu Arg Thr Leu Tyr Cys His Val
 1               5                  10                  15

<210> SEQ ID NO 7
<211> LENGTH: 16
<212> TYPE: PRT
<213> ORGANISM: Artificial Sequence
<220> FEATURE:
<223> OTHER INFORMATION: IGF1R binding peptide from pIX library

<400> SEQUENCE: 7

His Thr Cys Phe Tyr Pro Thr Leu Met Pro Pro Glu Leu Cys Phe Asp
 1               5                  10                  15

<210> SEQ ID NO 8
<211> LENGTH: 16
<212> TYPE: PRT
<213> ORGANISM: Artificial Sequence
```

```
<220> FEATURE:
<223> OTHER INFORMATION: IGF1R binding peptide from pIX library

<400> SEQUENCE: 8

Ser Asn Cys Pro Pro Leu Asp Met Arg Leu Thr Glu Leu Cys Val Met
1               5                   10                  15

<210> SEQ ID NO 9
<211> LENGTH: 23
<212> TYPE: PRT
<213> ORGANISM: Artificial Sequence
<220> FEATURE:
<223> OTHER INFORMATION: IGF1R binding peptide from pIX library

<400> SEQUENCE: 9

Trp His Cys Thr Pro Leu Thr Gln Ile Ala Asp Pro Gly Ser Ile Ile
1               5                   10                  15

His Ile Leu Glu Cys Thr Val
            20

<210> SEQ ID NO 10
<211> LENGTH: 24
<212> TYPE: PRT
<213> ORGANISM: Artificial Sequence
<220> FEATURE:
<223> OTHER INFORMATION: IGF1R binding peptide from pIX library

<400> SEQUENCE: 10

Val Glu Cys Asp Thr Pro Ser Ile Thr Phe Ser Pro Gly Leu Glu Ala
1               5                   10                  15

Leu Phe Trp Asn Thr Cys Ser Pro
            20

<210> SEQ ID NO 11
<211> LENGTH: 24
<212> TYPE: PRT
<213> ORGANISM: Artificial Sequence
<220> FEATURE:
<223> OTHER INFORMATION: IGF1R binding peptide from pIX library

<400> SEQUENCE: 11

Met Thr Cys Ala Trp His Thr Leu His Thr Asp Pro Gly Leu Thr Pro
1               5                   10                  15

Gln Leu Thr Leu Pro Cys Ile Tyr
            20

<210> SEQ ID NO 12
<211> LENGTH: 24
<212> TYPE: PRT
<213> ORGANISM: Artificial Sequence
<220> FEATURE:
<223> OTHER INFORMATION: IGF1R binding peptide from pIX library

<400> SEQUENCE: 12

Ala Gly Cys Pro Ser Pro Met Pro Pro Val Asp Pro Gly Phe Tyr Ser
1               5                   10                  15

Ala Ile Val Gln Leu Cys Arg Glu
            20

<210> SEQ ID NO 13
<211> LENGTH: 18
<212> TYPE: PRT
<213> ORGANISM: Artificial Sequence
<220> FEATURE:
<223> OTHER INFORMATION: IGF1R binding peptide from pIX library
```

-continued

```
<400> SEQUENCE: 13

Asp Asp Ile Asp Glu Phe Leu His Gln Leu His Asn Leu Val Asn Asn
 1               5                  10                  15

Val His

<210> SEQ ID NO 14
<211> LENGTH: 42
<212> TYPE: DNA
<213> ORGANISM: Artificial Sequence
<220> FEATURE:
<223> OTHER INFORMATION: DNA encoding IGF1R binding peptide from pIX
      library

<400> SEQUENCE: 14 acggggttgtg attttccgga gttgtgtcgt ggttgtcatc cg                    42

<210> SEQ ID NO 15
<211> LENGTH: 45
<212> TYPE: DNA
<213> ORGANISM: Artificial Sequence
<220> FEATURE:
<223> OTHER INFORMATION: DNA encoding IGF1R binding peptide from pIX
      library

<400> SEQUENCE: 15
gctgagtgtg agtggccgtg gcttacgctg gagctttgtc agtct                  45

<210> SEQ ID NO 16
<211> LENGTH: 45
<212> TYPE: DNA
<213> ORGANISM: Artificial Sequence
<220> FEATURE:
<223> OTHER INFORMATION: DNA encoding IGF1R binding peptide from pIX
      library

<400> SEQUENCE: 16 ccttttttgtt attctggtgg gccgctgccg tatccttgta cgtat                 45

<210> SEQ ID NO 17
<211> LENGTH: 45
<212> TYPE: DNA
<213> ORGANISM: Artificial Sequence
<220> FEATURE:
<223> OTHER INFORMATION: DNA encoding IGF1R binding peptide from pIX
      library

<400> SEQUENCE: 17
cctgtgtgtc cgtcgttttg ttatgatcag tatgtgtgtc cgact                  45

<210> SEQ ID NO 18
<211> LENGTH: 45
<212> TYPE: DNA
<213> ORGANISM: Artificial Sequence
<220> FEATURE:
<223> OTHER INFORMATION: DNA encoding IGF1R binding peptide from pIX
      library

<400> SEQUENCE: 18
tttacgtgtg ctgtttattc gttgtctgag ctggattgta gggat                  45

<210> SEQ ID NO 19
<211> LENGTH: 45
<212> TYPE: DNA
<213> ORGANISM: Artificial Sequence
<220> FEATURE:
<223> OTHER INFORMATION: DNA encoding IGF1R binding peptide from pIX
      library
```

```
<400> SEQUENCE: 19
ttgagttgtt atgatccgac gctgcgtacg ttgtattgtc atgtt            45

<210> SEQ ID NO 20
<211> LENGTH: 48
<212> TYPE: DNA
<213> ORGANISM: Artificial Sequence
<220> FEATURE:
<223> OTHER INFORMATION: DNA encoding IGF1R binding peptide from pIX
      library

<400> SEQUENCE: 20
catacgtgtt tttatcctac gctgatgcct cctgagctgt gtttcgat         48

<210> SEQ ID NO 21
<211> LENGTH: 48
<212> TYPE: DNA
<213> ORGANISM: Artificial Sequence
<220> FEATURE:
<223> OTHER INFORMATION: DNA encoding IGF1R binding peptide from pIX
      library

<400> SEQUENCE: 21
agtaattgtc ctccgttgga tatgcggctg actgagcttt gtgttatg         48

<210> SEQ ID NO 22
<211> LENGTH: 72
<212> TYPE: DNA
<213> ORGANISM: Artificial Sequence
<220> FEATURE:
<223> OTHER INFORMATION: DNA encoding IGF1R binding peptide from pIX
      library

<400> SEQUENCE: 22
tggcattgta ctccgctgac gcagattgct gatccaggcc agagtattat tcatattttg    60
gagtgtactg tt                                                        72

<210> SEQ ID NO 23
<211> LENGTH: 72
<212> TYPE: DNA
<213> ORGANISM: Artificial Sequence
<220> FEATURE:
<223> OTHER INFORMATION: DNA encoding IGF1R binding peptide from pIX
      library

<400> SEQUENCE: 23
gttgagtgtg atacgccgtc tattactttt tcgccaggcc tggaggcgct gttttggaat    60
acgtgttctc ct                                                        72

<210> SEQ ID NO 24
<211> LENGTH: 72
<212> TYPE: DNA
<213> ORGANISM: Artificial Sequence
<220> FEATURE:
<223> OTHER INFORMATION: DNA encoding IGF1R binding peptide from pIX
      library

<400> SEQUENCE: 24
atgacgtgtg cgtggcatac tttgcatacg gatccaggcc ttactccgca gctgaggctg    60
ccttgtattt at                                                        72

<210> SEQ ID NO 25
<211> LENGTH: 72
<212> TYPE: DNA
```

-continued

<213> ORGANISM: Artificial Sequence
<220> FEATURE:
<223> OTHER INFORMATION: DNA encoding IGF1R binding peptide from pIX
      library

<400> SEQUENCE: 25
gcggggtgtc cgagtccgat gccgccggtg gatccaggct tttatagtgc tattgtgcag      60
ctgtgtaggg ag                                                          72

<210> SEQ ID NO 26
<211> LENGTH: 54
<212> TYPE: DNA
<213> ORGANISM: Artificial Sequence
<220> FEATURE:
<223> OTHER INFORMATION: DNA encoding IGF1R binding peptide from pIX
      library

<400> SEQUENCE: 26
gatgacatag acgaatttct tcatcaactc cacaacctag taaacaatgt tcac            54

<210> SEQ ID NO 27
<211> LENGTH: 1367
<212> TYPE: PRT
<213> ORGANISM: Homo sapiens

<400> SEQUENCE: 27

Met Lys Ser Gly Ser Gly Gly Gly Ser Pro Thr Ser Leu Trp Gly Leu
 1               5                  10                  15

Leu Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
        35                  40                  45

Leu Glu Asn Cys Thr Val Ile Glu Gly Tyr Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

```
Ala Gly Val Cys Val Pro Ala Cys Pro Pro Asn Thr Tyr Arg Phe Glu
            260             265             270

Gly Trp Arg Cys Val Asp Arg Asp Phe Cys Ala Asn Ile Leu Ser Ala
        275             280             285

Glu Ser Ser Asp Ser Glu Gly Phe Val Ile His Asp Gly Glu Cys Met
    290             295             300

Gln Glu Cys Pro Ser Gly Phe Ile Arg Asn Gly Ser Gln Ser Met Tyr
305             310             315                         320

Cys Ile Pro Cys Glu Gly Pro Cys Pro Lys Val Cys Glu Glu Glu Lys
                325             330             335

Lys Thr Lys Thr Ile Asp Ser Val Thr Ser Ala Gln Met Leu Gln Gly
            340             345             350

Cys Thr Ile Phe Lys Gly Asn Leu Leu Ile Asn Ile Arg Arg Gly Asn
        355             360             365

Asn Ile Ala Ser Glu Leu Glu Asn Phe Met Gly Leu Ile Glu Val Val
    370             375             380

Thr Gly Tyr Val Lys Ile Arg His Ser His Ala Leu Val Ser Leu Ser
385             390             395                         400

Phe Leu Lys Asn Leu Arg Leu Ile Leu Gly Glu Glu Gln Leu Glu Gly
                405             410             415

Asn Tyr Ser Phe Tyr Val Leu Asp Asn Gln Asn Leu Gln Gln Leu Trp
            420             425             430

Asp Trp Asp His Arg Asn Leu Thr Ile Lys Ala Gly Lys Met Tyr Phe
        435             440             445

Ala Phe Asn Pro Lys Leu Cys Val Ser Glu Ile Tyr Arg Met Glu Glu
    450             455             460

Val Thr Gly Thr Lys Gly Arg Gln Ser Lys Gly Asp Ile Asn Thr Arg
465             470             475                         480

Asn Asn Gly Glu Arg Ala Ser Cys Glu Ser Asp Val Leu His Phe Thr
                485             490             495

Ser Thr Thr Thr Ser Lys Asn Arg Ile Ile Ile Thr Trp His Arg Tyr
            500             505             510

Arg Pro Pro Asp Tyr Arg Asp Leu Ile Ser Phe Thr Val Tyr Tyr Lys
        515             520             525

Glu Ala Pro Phe Lys Asn Val Thr Glu Tyr Asp Gly Gln Asp Ala Cys
    530             535             540

Gly Ser Asn Ser Trp Asn Met Val Asp Val Asp Leu Pro Pro Asn Lys
545             550             555                         560

Asp Val Glu Pro Gly Ile Leu Leu His Gly Leu Lys Pro Trp Thr Gln
                565             570             575

Tyr Ala Val Tyr Val Lys Ala Val Thr Leu Thr Met Val Glu Asn Asp
            580             585             590

His Ile Arg Gly Ala Lys Ser Glu Ile Leu Tyr Ile Arg Thr Asn Ala
        595             600             605

Ser Val Pro Ser Ile Pro Leu Asp Val Leu Ser Ala Ser Asn Ser Ser
    610             615             620

Ser Gln Leu Ile Val Lys Trp Asn Pro Pro Ser Leu Pro Asn Gly Asn
625             630             635                         640

Leu Ser Tyr Tyr Ile Val Arg Trp Gln Arg Gln Pro Gln Asp Gly Tyr
                645             650             655

Leu Tyr Arg His Asn Tyr Cys Ser Lys Asp Lys Ile Pro Ile Arg Lys
            660             665             670

Tyr Ala Asp Gly Thr Ile Asp Ile Glu Glu Val Thr Glu Asn Pro Lys
        675             680             685
```

-continued

```
Thr Glu Val Cys Gly Gly Glu Lys Gly Pro Cys Cys Ala Cys Pro Lys
    690                 695                 700
Thr Glu Ala Glu Lys Gln Ala Glu Lys Glu Glu Ala Glu Tyr Arg Lys
705                 710                 715                 720
Val Phe Glu Asn Phe Leu His Asn Ser Ile Phe Val Pro Arg Pro Glu
                725                 730                 735
Arg Lys Arg Arg Asp Val Met Gln Val Ala Asn Thr Thr Met Ser Ser
            740                 745                 750
Arg Ser Arg Asn Thr Thr Ala Ala Asp Thr Tyr Asn Ile Thr Asp Pro
    755                 760                 765
Glu Glu Leu Glu Thr Glu Tyr Pro Phe Phe Glu Ser Arg Val Asp Asn
    770                 775                 780
Lys Glu Arg Thr Val Ile Ser Asn Leu Arg Pro Phe Thr Leu Tyr Arg
785                 790                 795                 800
Ile Asp Ile His Ser Cys Asn His Glu Ala Glu Lys Leu Gly Cys Ser
                805                 810                 815
Ala Ser Asn Phe Val Phe Ala Arg Thr Met Pro Ala Glu Gly Ala Asp
            820                 825                 830
Asp Ile Pro Gly Pro Val Thr Trp Glu Pro Arg Pro Glu Asn Ser Ile
    835                 840                 845
Phe Leu Lys Trp Pro Glu Pro Glu Asn Pro Asn Gly Leu Ile Leu Met
    850                 855                 860
Tyr Glu Ile Lys Tyr Gly Ser Gln Val Glu Asp Gln Arg Glu Cys Val
865                 870                 875                 880
Ser Arg Gln Glu Tyr Arg Lys Tyr Gly Gly Ala Lys Leu Asn Arg Leu
                885                 890                 895
Asn Pro Gly Asn Tyr Thr Ala Arg Ile Gln Ala Thr Ser Leu Ser Gly
            900                 905                 910
Asn Gly Ser Trp Thr Asp Pro Val Phe Phe Tyr Val Gln Ala Lys Thr
    915                 920                 925
Gly Tyr Glu Asn Phe Ile His Leu Ile Ile Ala Leu Pro Val Ala Val
    930                 935                 940
Leu Leu Ile Val Gly Gly Leu Val Ile Met Leu Tyr Val Phe His Arg
945                 950                 955                 960
Lys Arg Asn Asn Ser Arg Leu Gly Asn Gly Val Leu Tyr Ala Ser Val
                965                 970                 975
Asn Pro Glu Tyr Phe Ser Ala Ala Asp Val Tyr Val Pro Asp Glu Trp
            980                 985                 990
Glu Val Ala Arg Glu Lys Ile Thr Met Ser Arg Glu Leu Gly Gln Gly
    995                 1000                1005
Ser Phe Gly Met Val Tyr Glu Gly Val Ala Lys Gly Val Val Lys Asp
    1010                1015                1020
Glu Pro Glu Thr Arg Val Ala Ile Lys Thr Val Asn Glu Ala Ala Ser
1025                1030                1035                1040
Met Arg Glu Arg Ile Glu Phe Leu Asn Glu Ala Ser Val Met Lys Glu
                1045                1050                1055
Phe Asn Cys His His Val Val Arg Leu Leu Gly Val Val Ser Gln Gly
            1060                1065                1070
Gln Pro Thr Leu Val Ile Met Glu Leu Met Thr Arg Gly Asp Leu Lys
    1075                1080                1085
Ser Tyr Leu Arg Ser Leu Arg Pro Glu Met Glu Asn Asn Pro Val Leu
    1090                1095                1100
Ala Pro Pro Ser Leu Ser Lys Met Ile Gln Met Ala Gly Glu Ile Ala
```

```
                1105                1110                1115                1120
Asp Gly Met Ala Tyr Leu Asn Ala Asn Lys Phe Val His Arg Asp Leu
                    1125                1130                1135
Ala Ala Arg Asn Cys Met Val Ala Glu Asp Phe Thr Val Lys Ile Gly
            1140                1145                1150
Asp Phe Gly Met Thr Arg Asp Ile Tyr Glu Thr Asp Tyr Tyr Arg Lys
        1155                1160                1165
Gly Gly Lys Gly Leu Leu Pro Val Arg Trp Met Ser Pro Glu Ser Leu
    1170                1175                1180
Lys Asp Gly Val Phe Thr Thr Tyr Ser Asp Val Trp Ser Phe Gly Val
1185                1190                1195                1200
Val Leu Trp Glu Ile Ala Thr Leu Ala Glu Gln Pro Tyr Gln Gly Leu
                1205                1210                1215
Ser Asn Glu Gln Val Leu Arg Phe Val Met Glu Gly Gly Leu Leu Asp
                    1220                1225                1230
Lys Pro Asp Asn Cys Pro Asp Met Leu Phe Glu Leu Met Arg Met Cys
            1235                1240                1245
Trp Gln Tyr Asn Pro Lys Met Arg Pro Ser Phe Leu Glu Ile Ile Ser
        1250                1255                1260
Ser Ile Lys Glu Glu Met Glu Pro Gly Phe Arg Glu Val Ser Phe Tyr
1265                1270                1275                1280
Tyr Ser Glu Glu Asn Lys Leu Pro Glu Pro Glu Glu Leu Asp Leu Glu
                1285                1290                1295
Pro Glu Asn Met Glu Ser Val Pro Leu Asp Pro Ser Ala Ser Ser Ser
                    1300                1305                1310
Ser Leu Pro Leu Pro Asp Arg His Ser Gly His Lys Ala Glu Asn Gly
            1315                1320                1325
Pro Gly Pro Gly Val Leu Val Leu Arg Ala Ser Phe Asp Glu Arg Gln
        1330                1335                1340
Pro Tyr Ala His Met Asn Gly Gly Arg Lys Asn Glu Arg Ala Leu Pro
1345                1350                1355                1360
Leu Pro Gln Ser Ser Thr Cys
                1365

<210> SEQ ID NO 28
<211> LENGTH: 8
<212> TYPE: PRT
<213> ORGANISM: Artificial Sequence
<220> FEATURE:
<223> OTHER INFORMATION: Linker

<400> SEQUENCE: 28

Gly Gly Gly Ser Gly Gly Gly Ser
 1               5

<210> SEQ ID NO 29
<211> LENGTH: 15
<212> TYPE: PRT
<213> ORGANISM: Artificial Sequence
<220> FEATURE:
<223> OTHER INFORMATION: Linker

<400> SEQUENCE: 29

Gly Gly Gly Gly Ser Gly Gly Gly Gly Ser Gly Gly Gly Gly Ser
 1               5                   10                  15

<210> SEQ ID NO 30
<211> LENGTH: 921
<212> TYPE: PRT
```

<213> ORGANISM: Artificial Sequence
<220> FEATURE:
<223> OTHER INFORMATION: variant of alkaline phosphatase

<400> SEQUENCE: 30

```
Thr Pro Glu Met Pro Val Leu Glu Asn Arg Ala Ala Gln Gly Asp Ile
 1               5                  10                  15

Thr Thr Pro Gly Gly Ala Arg Arg Leu Thr Gly Asp Gln Thr Ala Ala
            20                  25                  30

Leu Arg Asp Ser Leu Ser Asp Lys Pro Ala Lys Asn Ile Ile Leu Leu
        35                  40                  45

Ile Gly Asp Gly Met Gly Asp Ser Glu Ile Thr Ala Ala Arg Asn Tyr
 50                  55                  60

Ala Glu Gly Ala Gly Gly Phe Phe Lys Gly Ile Asp Ala Leu Pro Leu
 65                  70                  75                  80

Thr Gly Gln Tyr Thr His Tyr Ala Leu Asn Lys Lys Thr Gly Lys Pro
                85                  90                  95

Asp Tyr Val Thr Asp Ser Ala Ala Ser Ala Thr Ala Trp Ser Thr Gly
            100                 105                 110

Val Lys Thr Tyr Asn Gly Ala Leu Gly Val Asp Ile His Glu Lys Asp
        115                 120                 125

His Pro Thr Ile Leu Glu Met Ala Lys Ala Ala Gly Leu Ala Thr Gly
130                 135                 140

Asn Val Ser Thr Ala Glu Leu Gln Gly Ala Thr Pro Ala Ala Leu Val
145                 150                 155                 160

Ala His Val Thr Ser Arg Lys Cys Tyr Gly Pro Ser Ala Thr Ser Glu
                165                 170                 175

Lys Cys Pro Gly Asn Ala Leu Glu Lys Gly Gly Lys Gly Ser Ile Thr
            180                 185                 190

Glu Gln Leu Leu Asn Ala Arg Ala Asp Val Thr Leu Gly Gly Gly Ala
        195                 200                 205

Lys Thr Phe Ala Glu Thr Ala Thr Ala Gly Glu Trp Gln Gly Lys Thr
210                 215                 220

Leu Arg Glu Gln Ala Gln Thr Arg Gly Tyr Gln Leu Val Ser Asp Ala
225                 230                 235                 240

Ala Ser Leu Asn Ser Val Thr Glu Ala Asn Gln Gln Lys Pro Leu Leu
                245                 250                 255

Gly Leu Phe Ala Asp Gly Asn Met Pro Val Arg Trp Leu Gly Pro Lys
            260                 265                 270

Ala Thr Tyr His Gly Asn Ile Asp Lys Pro Ala Val Thr Cys Thr Pro
        275                 280                 285

Asn Pro Gln Arg Asn Asp Ser Val Pro Thr Leu Ala Gln Met Thr Asp
290                 295                 300

Lys Ala Ile Glu Leu Leu Ser Lys Asn Glu Lys Gly Phe Phe Leu Gln
305                 310                 315                 320

Val Glu Gly Ala Ser Ile Asp Lys Gln Asn His Ala Ala Asn Pro Cys
                325                 330                 335

Gly Gln Ile Gly Glu Thr Val Asp Leu Asp Glu Ala Val Gln Arg Ala
            340                 345                 350

Leu Glu Phe Ala Lys Lys Glu Gly Asn Thr Leu Val Ile Val Thr Ala
        355                 360                 365

Asp His Ala His Ala Ser Gln Ile Val Ala Pro Asp Thr Lys Ala Pro
370                 375                 380

Gly Leu Thr Gln Ala Leu Asn Thr Lys Asp Gly Ala Val Met Val Met
385                 390                 395                 400
```

```
Ser Tyr Gly Asn Ser Glu Glu Asp Ser Gln Glu His Thr Gly Ser Gln
                405                 410                 415

Leu Arg Ile Ala Ala Tyr Gly Pro His Ala Ala Asn Val Val Gly Leu
            420                 425                 430

Thr Asp Gln Thr Asp Leu Phe Tyr Thr Met Lys Ala Ala Leu Gly Leu
            435                 440                 445

Lys Val Pro Gly Gly Ser Gly Gly Ser Gly Gly Gly Ser Gly Gly
        450                 455                 460

Gly Ser Gly Thr Pro Glu Met Pro Val Leu Glu Asn Arg Ala Ala Gln
465                 470                 475                 480

Gly Asp Ile Thr Thr Pro Gly Gly Ala Arg Arg Leu Thr Asp Gln
            485                 490                 495

Thr Ala Ala Leu Arg Asp Ser Leu Ser Asp Lys Pro Ala Lys Asn Ile
            500                 505                 510

Ile Leu Leu Ile Gly Asp Gly Met Gly Asp Ser Glu Ile Thr Ala Ala
            515                 520                 525

Arg Asn Tyr Ala Glu Gly Ala Gly Gly Phe Phe Lys Gly Ile Asp Ala
            530                 535                 540

Leu Pro Leu Thr Gly Gln Tyr Thr His Tyr Ala Leu Asn Lys Lys Thr
545                 550                 555                 560

Gly Lys Pro Asp Tyr Val Thr Asp Ser Ala Ala Ser Ala Thr Ala Trp
                565                 570                 575

Ser Thr Gly Val Lys Thr Tyr Asn Gly Ala Leu Gly Val Asp Ile His
            580                 585                 590

Glu Lys Asp His Pro Thr Ile Leu Glu Met Ala Lys Ala Ala Gly Leu
            595                 600                 605

Ala Thr Gly Asn Val Ser Thr Ala Glu Leu Gln Gly Ala Thr Pro Ala
            610                 615                 620

Ala Leu Val Ala His Val Thr Ser Arg Lys Cys Tyr Gly Pro Ser Ala
625                 630                 635                 640

Thr Ser Glu Lys Cys Pro Gly Asn Ala Leu Glu Lys Gly Gly Lys Gly
                645                 650                 655

Ser Ile Thr Glu Gln Leu Leu Asn Ala Arg Ala Asp Val Thr Leu Gly
            660                 665                 670

Gly Gly Ala Lys Thr Phe Ala Glu Thr Ala Thr Ala Gly Glu Trp Gln
            675                 680                 685

Gly Lys Thr Leu Arg Glu Gln Ala Gln Thr Arg Gly Tyr Gln Leu Val
        690                 695                 700

Ser Asp Ala Ala Ser Leu Asn Ser Val Thr Glu Ala Asn Gln Gln Lys
705                 710                 715                 720

Pro Leu Leu Gly Leu Phe Ala Asp Gly Asn Met Pro Val Arg Trp Leu
                725                 730                 735

Gly Pro Lys Ala Thr Tyr His Gly Asn Ile Asp Lys Pro Ala Val Thr
            740                 745                 750

Cys Thr Pro Asn Pro Gln Arg Asn Asp Ser Val Pro Thr Leu Ala Gln
            755                 760                 765

Met Thr Asp Lys Ala Ile Glu Leu Leu Ser Lys Asn Glu Lys Gly Phe
        770                 775                 780

Phe Leu Gln Val Glu Gly Ala Ser Ile Asp Lys Gln Asn His Ala Ala
785                 790                 795                 800

Asn Pro Cys Gly Gln Ile Gly Glu Thr Val Asp Leu Asp Glu Ala Val
                805                 810                 815

Gln Arg Ala Leu Glu Phe Ala Lys Lys Glu Gly Asn Thr Leu Val Ile
```

-continued

```
                   820             825             830
Val Thr Ala Asp His Ala His Ala Ser Gln Ile Val Ala Pro Asp Thr
            835             840             845

Lys Ala Pro Gly Leu Thr Gln Ala Leu Asn Thr Lys Asp Gly Ala Val
    850             855             860

Met Val Met Ser Tyr Gly Asn Ser Glu Glu Asp Ser Gln Glu His Thr
865             870             875             880

Gly Ser Gln Leu Arg Ile Ala Ala Tyr Gly Pro His Ala Ala Asn Val
            885             890             895

Val Gly Leu Thr Asp Gln Thr Asp Leu Phe Tyr Thr Met Lys Ala Ala
            900             905             910

Leu Gly Leu Lys Val Pro Gly Asn Ser
        915             920

<210> SEQ ID NO 31
<211> LENGTH: 54
<212> TYPE: PRT
<213> ORGANISM: Unknown
<220> FEATURE:
<223> OTHER INFORMATION: Protein G from unknown bacteria

<400> SEQUENCE: 31

Tyr Lys Leu Ile Leu Asn Gly Lys Thr Leu Lys Gly Glu Thr Thr Thr
1               5                   10                  15

Glu Ala Val Asp Ala Ala Thr Ala Glu Lys Val Phe Lys Gln Tyr Ala
            20              25                  30

Asn Asp Asn Gly Val Asp Gly Glu Trp Thr Tyr Asp Asp Ala Thr Lys
        35              40                  45

Thr Phe Thr Val Thr Glu
    50
```

INSULIN-LIKE GROWTH FACTOR 1 RECEPTOR BINDING PEPTIDES

CROSS-REFERENCE TO RELATED APPLICATIONS

This application claims the benefit of U.S. Provisional Application Ser. No. 61/348,937, filed 27 May 2010, the entire contents of which is incorporated herein by reference in its entirety.

FIELD OF THE INVENTION

The present invention relates to insulin-like growth factor 1 receptor binding peptides, polynucleotides encoding them, and methods of making and using the foregoing.

BACKGROUND OF THE INVENTION

Recent advances in biomedical research and high-throughput drug screening have generated numerous potential therapeutics for the treatment of CNS related illnesses. However, many therapeutics fail in vivo testing because of inadequate transport through the blood-brain barrier (BBB).

Therapeutics can cross the BBB using several pathways, including saturable transporter systems, adsorptive transcytosis wherein the therapeutic to be transported is internalized by a cell in the BBB and routed to the abluminal surface for deposition into the brain intracellular fluid compartment, transmembrane diffusion wherein the therapeutic dissolves into the lipid bilayer which forms the membranes of the cells comprising the BBB, and extracellular pathways wherein the therapeutic exploits the residual leakiness of the BBB.

Several approaches to modify therapeutic agents to alter their BBB permeability have been attempted, including conjugation with proteins that naturally cross the BBB, for example insulin, insulin-growth factor 1 and 2 (IGF-1, IGF-2), leptin and transferrin (US Pat. Appl. No. US2007/0081992), linking the polypeptides to cationized antibodies binding to certain cellular receptors, such as insulin receptor (U.S. Pat. No. 7,388,079) or transferrin receptor (U.S. Pat. No. 6,329,508; Zhang and Pardridge, Brain Res. 889:49-56, 2001); coupling the therapeutics with synthetic polymers such as poly(butyl cyanoacrylate) or polyacrylamide covered with Polysorbate 80 (US Pat. Appl. No. 2002/0009491, US Pat. Appl. No. 2002/0013266; US Pat. Appl. No. 2006/0051317), and using liposomes or immunoliposomes.

The current approaches to improve the transport of therapeutic agents across the BBB include ineffectiveness due to competition with the endogenous ligand, lack of transport of the therapeutic to brain parenchyma, and degradation of the therapeutics due to lysosomal targeting.

Thus, there is a need to develop methods to transport therapeutic agents through the BBB.

SUMMARY OF THE INVENTION

One aspect of the invention is an isolated polypeptide comprising a polypeptide having the sequence shown in SEQ ID NOs: 1-13.

Another aspect of the invention is an isolated polynucleotide comprising a polynucleotide encoding the polypeptide comprising the amino acid sequence shown in SEQ ID NOs: 1-13.

Another aspect of the invention is an isolated polynucleotide comprising a polynucleotide having the sequence shown in SEQ ID NOs: 14-26, or a complementary sequence thereof.

Another aspect of the invention is an isolated vector comprising a polynucleotide having the sequence shown in SEQ ID NOs: 14-26.

Another aspect of the invention is an isolated host cell comprising the vector of the invention.

Another aspect of the invention is an isolated fusion protein comprising a polypeptide having the sequence shown in SEQ ID NOs: 1-13 fused to a second polypeptide.

Another aspect of the invention is a method of expressing a polypeptide comprising the steps of:
  a. providing the host cell of the invention; and
  b. culturing the host cell under conditions sufficient for the expression of the polypeptide having the sequence shown in SEQ ID NOs: 1-13.

Another aspect of the invention is a method for delivery of a therapeutic agent across endothelial cells, comprising
  a. conjugating the therapeutic agent to a polypeptide comprising the polypeptide having the sequence shown in SEQ ID NOs: 1, 2, 4, 8, or 12 to form a conjugate;
  b. contacting the conjugate with the endothelial cells; and
  c. measuring the amount of the conjugate delivered across the endothelial cells.

DETAILED DESCRIPTION OF THE INVENTION

All publications, including but not limited to patents and patent applications, cited in this specification are herein incorporated by reference as though fully set forth.

As used herein and in the claims, the singular forms "a," "and," and "the" include plural reference unless the context clearly dictates otherwise. Thus, for example, reference to "a polypeptide" is a reference to one or more polypeptides and includes equivalents thereof known to those skilled in the art.

Unless defined otherwise, all technical and scientific terms used herein have the same meaning as commonly understood by one of ordinary skill in the art to which an invention belongs. Although any compositions and methods similar or equivalent to those described herein can be used in the practice or testing of the invention, exemplary compositions and methods are described herein.

The term "polypeptide" means a molecule that comprises at least two amino acid residues linked by a peptide bond to form a polypeptide. Small polypeptides of less than 50 amino acids may be referred to as "peptides". Polypeptides may also be referred as "proteins."

The term "polynucleotide" means a molecule comprising a chain of nucleotides covalently linked by a sugar-phosphate backbone or other equivalent covalent chemistry. Double and single-stranded DNAs and RNAs are typical examples of polynucleotides.

The term "complementary sequence" means a second isolated polynucleotide sequence that is antiparallel to a first isolated polynucleotide sequence and that comprises nucleotides complementary to the nucleotides in the first polynucleotide sequence. Typically, such "complementary sequences" are capable of forming a double-stranded polynucleotide molecule such as double-stranded DNA or double-stranded RNA when combined under appropriate conditions with the first isolated polynucleotide sequence.

The term "vector" means a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system. Examples of such biological systems may include a cell, virus, animal, plant, and reconstituted biological systems utilizing biological components capable of duplicating a vector. The polynucleotides comprising a vector may be DNA or RNA molecules or hybrids of these.

The term "expression vector" means a vector that can be utilized in a biological system or a reconstituted biological system to direct the translation of a polypeptide encoded by a polynucleotide sequence present in the expression vector.

The term "blood-brain barrier" or "BBB" as used herein refers to the barrier between the peripheral circulation and the brain and spinal cord which is formed by tight junctions within the brain capillary endothelial plasma membranes, creates an extremely tight barrier that restricts the transport of molecules into the brain, even molecules as small as urea having a molecular weight of 60 Da. The blood-brain barrier within the brain, the blood-spinal cord barrier within the spinal cord, and the blood-retinal barrier within the retina, are contiguous capillary barriers within the central nervous system (CNS), and are collectively referred to as the blood-brain barrier.

The term "antibody" refers to a molecule specifically binding to an antigen, and includes dimeric, trimeric and multimeric antibodies, and chimeric, humanized and fully human antibodies. Also, an antibody may be a whole antibody or a functional fragment of an antibody molecule, such as a fragment retaining at least its antigen binding function, and include Fab, F(ab'), F(ab')$_2$, scFv, dsFv, and diabodies. For example, antibody fragments may be obtained using proteolytic enzymes (e.g., a whole antibody is digested with papain to produce Fab fragments, and pepsin treatment results in the production of F(ab')$_2$ fragments). Techniques for the preparation and use of the various antibodies are well known in the art (Ausubel, et al., ed., Current Protocols in Molecular Biology, John Wiley & Sons, Inc., NY 1987-2001; Sambrook, et al., Molecular Cloning: A Laboratory Manual, $2^{nd}$ Edition, Cold Spring Harbor, N.Y., 1989; Harlow and Lane, Antibodies, a Laboratory Manual, Cold Spring Harbor, N.Y., 1989; Colligan, et al., ed., Current Protocols in Immunology, John Wiley & Sons, Inc., NY 1994-2001; Colligan et al., Current Protocols in Protein Science, John Wiley & Sons, NY, N.Y., 1997-2001; Kohler et al., Nature 256:495-497, 1975; U.S. Pat. No. 4,816,567, Queen et al., Proc. Natl. Acad. Sci. 86:10029-10033, 1989). For example, fully human monoclonal antibodies lacking any non-human sequences can be prepared from human immunoglobulin transgenic mice or from phage display libraries (Lonberg et al., Nature 368:856-859, 1994; Fishwild et al., Nature Biotech. 14:845-851, 1996; Mendez et al., Nature Genetics 15:146-156, 1997; Knappik et al., J. Mol. Biol. 296:57-86, 2000; Krebs et al., J. Immunol. Meth. 265:67-84, 2001).

An antibody molecule or preparation "specifically binds" a given antigen when it binds this antigen with higher affinity and in a specific, as opposed to non-specific fashion, relative to a second non-identical antigen. Stated differently, the "specific binding" of an antibody molecule or preparation can be used to distinguish between two different polypeptides.

The term "insulin-like growth factor receptor 1" or "IGF1R" as used herein refers to a human IGF1R (GenBank Acc. No. NP_000866) having an amino acid sequence shown in SEQ ID NO: 27. The IGF1R pro-polypeptide is cleaved into an alpha and a beta chain to form a mature protein. The alpha chain has amino acid residues 31-740 of SEQ ID NO: 27, and the beta chain has amino acid residues 741-1367 of SEQ ID NO: 27. "Soluble IGF1R" or "sIGF1R" as used herein refers to the extracellular domain of the IGF1R (amino acids 31-932 of SEQ ID NO: 27). The soluble IGF1R may be an extracellular domain of an uncleaved pro-polypeptide, or an extracellular domain of a mature IGF1R (amino acid residues 31-740 forming the alpha chain, and amino acid residues 741-932 forming the extracellular portion of the beta chain).

The term "conjugate" as used herein refers to a chimeric molecule comprising a peptide of the invention having an amino acid sequence shown in SEQ ID NOs: 1-13 and a therapeutic agent. The term "conjugated" or "conjugating" means that the therapeutic agent(s) and the peptides of the invention are physically linked by, for example, by covalent chemical bonds, physical forces such as van der Waals or hydrophobic interactions, encapsulation, embedding, or combinations thereof. The therapeutic agent(s) and the peptides of the invention can be linked by chemical bonds through alcohol, acid, carbonyl, thiol or amine groups using well known chemical synthesis methods (see e.g. US Pat. Appl. No. US2010/0028370). The therapeutic agent can be connected to the peptides of the invention by a linker. Exemplary linkers are glycine-rich linkers such as Gly$_3$SerGly$_3$Ser (SEQ ID NO: 28) or Gly$_4$SerGly$_4$SerGly$_4$Ser (SEQ ID NO: 29). When the therapeutic agent and the peptides of the invention are conjugated via a covalent bond or a peptide and the therapeutic agent is a polypeptide, then the entire conjugate is a "fusion protein". Thus, the term "fusion protein" refers to a polypeptide made up of two (or more) heterologous polypeptides which are not normally fused together in a single amino acid sequence. Fusion proteins may generally be prepared using either recombinant nucleic acid methods, i.e., as a result of transcription and translation of a recombinant gene fusion product, which fusion comprises a segment encoding a polypeptide of the invention and a segment encoding a heterologous polypeptide.

The term "therapeutic agent" as used herein refers to a molecule administered to induce a desired therapeutic effect in a subject. A subject is a human or non-human animal, including a mammal or a primate. Exemplary therapeutic agents are proteins, antibodies, peptides, small molecules, or polynucleotides. Therapeutic agents may also be toxins or radioisotopes, where the therapeutic effect intended is, for example, the killing of a cancer cell.

The present invention provides isolated polypeptides that bind IGF1R, polynucleotides encoding the polypeptides, vectors comprising the polynucleotides, isolated host cells, polypeptides obtainable from expression of the polynucleotides, methods for expressing the polypeptides of the invention, and methods of using the polynucleotides and polypeptides of the invention. The polypeptides of the invention bind to the IGF1R, and are transcytosed across endothelial cells. Since IFG1R is expressed on the endothelial cells within the blood-brain barrier (BBB), the polypeptides of the invention can provide means for delivering therapeutic agents across the BBB.

One aspect of the invention is an isolated polypeptide comprising a polypeptide having the sequence shown in SEQ ID NOs: 1-13.

The polypeptides of the invention may be produced by chemical synthesis, such as solid phase peptide synthesis, on an automated peptide synthesizer. Alternatively, the polypeptides of the invention can be obtained from polynucleotides encoding these polypeptides by the use of cell-free expression systems such as reticulocyte lysate based expression systems, wheat germ extract based expression systems, and *Escherichia coli* extract based expression systems. The polypeptides of the invention can also be obtained by expression and isolation from cells harboring a nucleic acid sequence of the invention by techniques well known in the art, such as recombinant expression of easily isolated affinity labeled polypeptides. Those skilled in the art will recognize other techniques for obtaining the polypeptides of the invention.

Another aspect of the invention is an isolated fusion protein comprising a polypeptide having the sequence shown in SEQ ID NOs: 1-13 fused to a second polypeptide. Such second polypeptide may be a leader or a secretory signal sequences. Such second polypeptide may be a therapeutic agent fused to the peptides of the invention. The therapeutic agent and the peptide of the invention can be fused to one another in a variety of ways. The C-terminus or the N-terminus of the peptide of the invention may be directly linked to the N-terminus or the C-terminus, respectively of the therapeutic agent via an amide bond or a peptide linker. Therapeutic agents may be linked to the peptide of the invention using chemical crosslinking well known in the art.

Another aspect of the invention is an isolated polynucleotide comprising a polynucleotide encoding the polypeptides of the invention.

The polynucleotides of the invention may be produced by chemical synthesis such as solid phase polynucleotide synthesis on an automated polynucleotide synthesizer. Alternatively, the polynucleotides of the invention may be produced by other techniques such as PCR based duplication, vector based duplication, or restriction enzyme based DNA manipulation techniques. Techniques for producing or obtaining polynucleotides of a given known sequence are well known in the art.

The polynucleotides of the invention may also comprise at least one non-coding sequence, such as transcribed but not translated sequences, termination signals, ribosome binding sites, mRNA stabilizing sequences, introns and polyadenylation signals. The polynucleotide sequences may also comprise additional sequences encoding additional amino acids. These additional polynucleotide sequences may, for example, encode a marker or tag sequence such as a hexa-histidine peptide (Gentz et al., Proc. Natl. Acad. Sci. (USA) 86:821-284, 1989) or the HA peptide tag (Wilson et al., Cell 37:767-778, 1984) which facilitate the purification of fused polypeptides. Exemplary polynucleotides are polynucleotides having a sequence shown in SEQ ID NOs: 14-26.

Another embodiment of the invention is a vector comprising an isolated polynucleotide having a sequence shown in SEQ ID NOs: 14-26. The vectors of the invention are useful for maintaining polynucleotides, duplicating polynucleotides, or driving expression of a polypeptide encoded by a vector of the invention in biological systems, including reconstituted biological systems. Vectors may be chromosomal-, episomal- and virus-derived such as vectors derived from bacterial plasmids, bacteriophages, transposons, yeast episomes, insertion elements, yeast chromosomal elements, baculoviruses, papova viruses such as SV40, vaccinia viruses, adenoviruses, fowl pox viruses, pseudorabies viruses, picornaviruses and retroviruses and vectors derived from combinations thereof, such as cosmids and phagemids.

The vectors of the invention can be formulated in microparticles, with adjuvants, lipid, buffer or other excipients as appropriate for a particular application.

In one embodiment of the invention the vector is an expression vector. Expression vectors typically comprise nucleic acid sequence elements that can control, regulate, cause or permit expression of a polypeptide encoded by such a vector. Such elements may comprise transcriptional enhancer binding sites, RNA polymerase initiation sites, ribosome binding sites, and other sites that facilitate the expression of encoded polypeptides in a given expression system. Such expression systems may be cell-based, or cell-free systems well known in the art. Nucleic acid sequence elements and parent vector sequences suitable for use in the expression of encoded polypeptides are also well known. An exemplary plasmid-derived expression vector useful for expression of the polypeptides of the invention comprises an *E. coli* origin of replication, a chloramphenicol acetyltransferase (CAT) gene, a bacteriophage T7 promoter, a pelB signal sequence, and a T7 terminator sequence.

Another embodiment of the invention is an isolated host cell comprising a vector of the invention. Representative host cell examples include Archaea cells; bacterial cells such as Streptococci, Staphylococci, Enterococci, *E. coli, Streptomyces*, cyanobacteria, *B. subtilis* and *S. aureus*; fungal cells such as *Kluveromyces, Saccharomyces*, Basidomycete, *Candida albicans* or *Aspergillus*; insect cells such as *Drosophila* S2 and *Spodoptera* Sf9; animal cells such as CHO, COS, HeLa, C127, 3T3, BHK, 293, CV-1, Bowes melanoma and myeloma; and plant cells, such as gymnosperm or angiosperm cells. The host cells in the methods of the invention may be provided as individual cells, or populations of cells. Populations of cells may comprise an isolated or cultured population of cells or cells present in a matrix such as a tissue.

Introduction of a polynucleotide, such as a vector, into a host cell can be effected by methods well known to those skilled in the art (Davis et al., Basic Methods in Molecular Biology, $2^{nd}$ ed., Appleton & Lange, Norwalk, Conn., 1994; $3^{rd}$ ed., Sambrook et al., Molecular Cloning: A Laboratory Manual, ed., Cold Spring Harbor Laboratory Press, Cold Spring Harbor, N.Y., 2001). These methods include calcium phosphate transfection, DEAE-Dextran mediated transfection, microinjection, cationic lipid-mediated transfection, electroporation, transduction, scrape loading, ballistic introduction and infection.

It is possible to modify the structure of the polypeptides or fragments of the invention for such purposes as enhancing substrate specificity, stability, solubility, and the like. For example, a modified polypeptide can be produced in which the amino acid sequence has been altered, such as by amino acid substitution, deletion, or addition. It is contemplated that an isolated replacement of a leucine with an isoleucine or valine, an aspartate with a glutamate, a threonine with a serine, or a similar replacement of an amino acid with a structurally related amino acid (i.e., conservative mutations) will, in some instances but not all, not have a major effect on the biological activity of the resulting molecule. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. Alternatively, the amino acid repertoire can be grouped as (1) acidic (aspartate, glutamate); (2) basic (lysine, arginine histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (Stryer (ed.), Biochemistry, 2nd ed, WH Freeman and Co., 1981). Whether a change in the amino acid sequence of a polypeptide or fragment thereof results in a functional homolog can be readily determined by assessing the ability of the modified polypeptide or fragment to produce a response in a fashion similar to the unmodified polypeptide or fragment using the assays described herein. Peptides, polypeptides or proteins in which more than one replacement has taken place can readily be tested in the same manner.

The polypeptides of the invention can also be formulated in a pharmaceutically acceptable carrier or diluent. A variety of aqueous carriers may be employed, e.g., 0.4% saline, 0.3% glycine and the like. These solutions are sterile and generally free of particulate matter. These solutions may be sterilized by conventional, well-known sterilization techniques (e.g., filtration). The compositions may contain pharmaceutically acceptable auxiliary substances as required to approximate physiological conditions, such as pH adjusting and buffering agents. The concentration of the polypeptides of the invention in such pharmaceutical formulation can vary widely, i.e., from less than about 0.5%, usually at or at least about 1% to as much as 15 or 20% by weight and will be selected primarily based on fluid volumes, viscosities and other factors, according to the particular mode of administration selected. The appropriate therapeutically effective dose can be determined readily by those of skill in the art. A determined dose may, if necessary, be repeated at appropriate time intervals selected as appropriate by a physician or other person skilled in the relevant art (e.g. nurse, veterinarian, or veterinary technician) during the treatment period.

The polypeptides of the invention can be lyophilized for storage and reconstituted in a suitable carrier prior to use. This technique has been shown to be effective with conventional protein preparations. Lyophilization and reconstitution techniques are well known in the art.

Another embodiment of the invention is a method for expressing a polypeptide comprising the steps of providing a host cell of the invention; culturing the host cell under conditions sufficient for the expression of at least one polypeptide of the invention.

Host cells can be cultured under any conditions suitable for maintaining or propagating a given type of host cell and sufficient for expressing a polypeptide. Culture conditions, media, and related methods sufficient for the expression of polypeptides are well known in the art. For example, many mammalian cell types can be aerobically cultured at 37° C. using appropriately buffered DMEM media while bacterial, yeast and other cell types may be cultured at 37° C. under appropriate atmospheric conditions in LB media.

In the methods of the invention the expression of a polypeptide can be confirmed using a variety of well known methods. For example, expression of a polypeptide can be confirmed using detection reagents, such as antibodies using for example FACS or immunofluorescent techniques, or using SDS-PAGE or HPLC.

Another aspect of the invention is a method for delivery of a therapeutic agent across endothelial cells, comprising:
  a. conjugating the therapeutic agent to a polypeptide comprising the polypeptide having the sequence shown in SEQ ID NOs: 1, 2, 4, 8, or 12 to form a conjugate;
  b. contacting the conjugate with the endothelial cells; and
  c. measuring the amount of the conjugate delivered across the endothelial cells.

The polypeptides of the invention facilitate delivery of a therapeutic agent across endothelial cells through the binding of the polypeptides of the invention to an IGF1R. The peptides are selected so that the conjugated therapeutic agent does not interfere with binding of the polypeptides of the invention to IGF1R. The present invention describes conjugation of a protein having a molecular weight of approximately 100 kD (921 amino acids) to the polypeptides of the invention without loss of transcytosis activity. Other polypeptides of comparable size are also likely to be successfully conjugated to the polypeptides of the invention and delivered across endothelial cell to the brain.

Delivery of the conjugate across the endothelial cells can be measured using well known in vitro or in vivo methods. Exemplary in vitro measurements can be done using polarized monolayers of endothelial cells and measuring the transcytosis of the conjugate using for example antibodies to the conjugate. In vivo measurements can be done in a subject using for example radioactive conjugates and measuring their distribution in brain after administration. Good correlation has been observed between the in vitro and in vivo method. For example, Perrier et al., demonstrated good correlation (R=0.94) between the permeability coefficients of a series of compounds and their corresponding in vivo rodent bloodbrain transfer coefficients using co-cultures of astrocytes and rat brain endothelial cells (Perrier et al., Brain Res. 1150:1-13, 2007).

The present invention will now be described with reference to the following specific, non-limiting examples.

Example 1

Identification of IGF1R Binding Peptides

Phage Panning

The pIX phage libraries displaying random peptides were generated according to methods described in US Pat. Appl. No. US2010/0021477, and used as a source of human IGF1R binding peptides. This library was panned in solution against a biotinylated form of purified soluble IGF1R (sIGF1R) having a carboxy-terminal hexahistidine tag (R&D Systems, Minneapolis, Minn.) for three rounds. Biotinylation of sIGF1R was done using the EZ-Link No-Weigh Sulfo-NHS-LC-Biotin Microtubes (Pierce, Rockford, Ill.). Because of the large size of sIGF1R (~330 kDa), Tetralink Avidin beads were used for round 1 selection due to their ~10 fold greater binding capacity than Dynal magnetic beads.

Total of 384 individual phage lysates from the panning were tested for binding specificity towards sIGF1R in a solid phase phage ELISA. Briefly, 100 μl/well of 5 μg/ml sIGF1R (R&D Systems, Minneapolis, Minn.) was bound to Black Maxisorp Plates (Nunc, Rochester, N.Y.), 25 μl of phage lysate added, and the reaction was detected using anti-M13-HRP antibody (EMD Biosciences, Gibbstown, N.J.) and POD substrate (Roche, Indianapolis, Ind.), and the signal detected using a TEKAN plate reader. A non-related protein demonstrated not to cross the BBB was used as a negative control. Positive lysates were defined as clones with a sIGF1R specific signal that was three fold above the background of the negative control. A total of 13 clones with unique peptide sequences were obtained with confirmed binding to the sIGF1R (Table 1). From these 13 clones, 3 (clones 5, 13 and 16) cross-reacted with the insulin receptor.

The peptides from clones 5-14, 16 and 17 were cloned in-frame as peptide-Alkaline phosphatase-His6 (peptide-AP) fusion proteins into a modified pET20b+ vector having a Chloramphenicol acetyltransferase (CAT) gene cloned within. The resulting peptide-AP fusions were expressed in bacteria and purified using Ni-NTA (EMD Biosciences, Gibbstown, N.J.) according to manufacturer's instructions. The amino acid sequence of the alkaline phosphatase used is shown in SEQ ID NO: 30.

TABLE 1a

Polypeptide sequences of identified IGF1R binding peptides

| Peptide Sequence | Clone number: | Peptide SEQ ID NO: |
|---|---|---|
| TGCDFPELCRGCHP | 5 | 1 |
| AECEWPWLTLELCQS | 6 | 2 |
| PFCYSGGPLPYPCTY | 7 | 3 |
| PVCPSFCYDQYVCPT | 8 | 4 |
| FTCAVYSLSELDCRD | 9 | 5 |
| LSCYDPTLRTLYCHV | 10 | 6 |
| HTCFYPTLMPPELCFD | 11 | 7 |
| SNCPPLDMRLTELCVM | 12 | 8 |
| WHCTPLTQIADPGSIIHILECW | 13 | 9 |
| VECDTPSITFSPGLEALFWNTCSP | 14 | 10 |
| MTCAWHTLHTDPGLTPQLTLPCIY | 15 | 11 |
| AGCPSPMPPVDPGFYSAIVQLCRE | 16 | 12 |
| DDIDEFLHQLHNLVNNVH | 17 | 13 |

Figure 1:
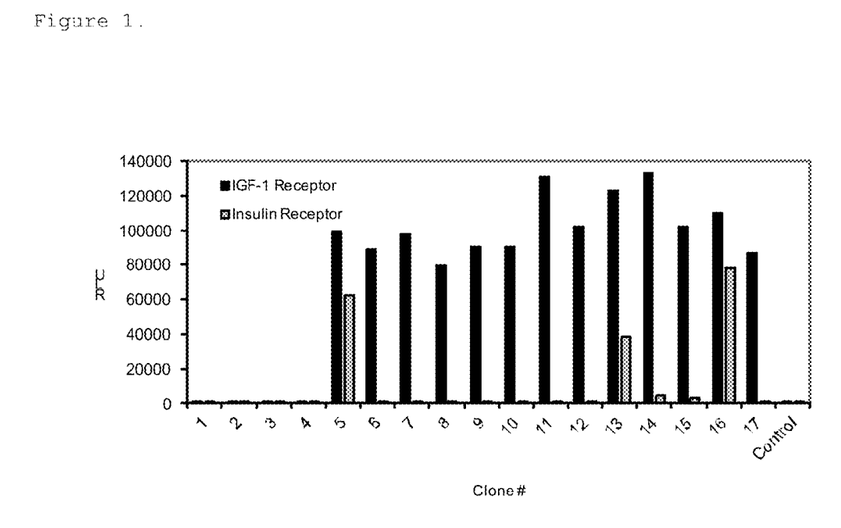
FIG. 1. shows binding of select phage lysates to IGF1R and IR.
Figure 2:
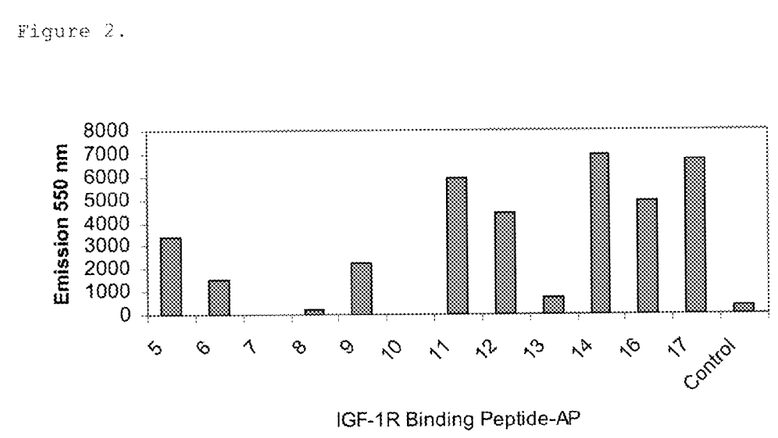
FIG. 2. shows binding of peptide-AP fusions to IGF1R.

The binding of purified peptide-AP fusion proteins to sIGF1R was assessed using ELISA against immobilized sIGF1R. Briefly, bacteria transformed with each peptide-AP fusion expression vector were grown overnight and the following day the cultures were clarified by centrifugation at 4,500 rpm, 4° C. The supernatants were collected and 75 µl of each supernatant was assayed for binding to 2 µg/ml sIGF1R immobilized on ELISA plates. The bound peptides were detected using the Attophos Substrate (Roche, Indianapolis, Ind.) following the manufacturer's recommendation and read using a Molecular Devices M5 plate reader. Fusions with peptide clones 7 and 10 did not express well. All other peptide-AP fusions showed binding activity to sIGF1R (FIG. 2).

TABLE 1b

Polynucleotide sequences of the IGF1R binding pepetides

| Clone number: | SEQ ID NO: | Sequence |
|---|---|---|
| 5 | 14 | ACGGGTTGTGATTTTCCGGAGTTGTGTCGT GGTTGTCATCCG |
| 6 | 15 | GCTGAGTGTGAGTGGCCGTGGCTTACGCTG GAGCTTTGTCAGTCT |
| 7 | 16 | CCTTTTTGTTATTCTGGTGGGCCGCTGCCG TATCCTTGTACGTAT |
| 8 | 17 | CCTGTGTGTCCGTCGTTTTGTTATGATCAG TATGTGTCCGACT |
| 9 | 18 | TTTACGTGTGCTGTTTATTCGTTGTCTGAG CTGGATTGTAGGGAT |
| 10 | 19 | TTGAGTTGTTATGATCCGACGCTGCGTACG TTGTATTGTCATGTT |
| 11 | 20 | CATACGTGTTTTTATCCTACGCTGATGCCT CCTGAGCTGTGTTTCGAT |
| 12 | 21 | AGTAATTGTCCTCCGTTGGATATGCGGCTG ACTGAGCTTTGTGTTATG |
| 13 | 22 | TGGCATTGTACTCCGCTGACGCAGATTGCT GATCCAGGCCAGAGTATTATTCATATTTTG GAGTGTACTGTT |

TABLE 1b-continued

Polynucleotide sequences of the IGF1R binding pepetides

| Clone number: | SEQ ID NO: | Sequence |
|---|---|---|
| 14 | 23 | GTTGAGTGTGATACGCCGTCTATTACTTTT TCGCCAGGCCTGGAGGCGCTGTTTTGGAAT ACGTGTTCTCCT |
| 15 | 24 | ATGACGTGTGCGTGGCATACTTTGCATACG GATCCAGGCCTTACTCCGCAGCTGAGGCTG CCTTGTATTTAT |
| 16 | 25 | GCGGGGTGTCCGAGTCCGATGCCGCCGGTG GATCCAGGCTTTTATAGTGCTATTGTGCAG CTGTGTAGGGAG |
| 17 | 26 | GATGACATAGACGAATTTCTTCATCAACTC CACAACCTAGTAAACAATGTTCAC |

Example 2

Characterization of the IGF1R Binding Peptides

The identified IFG1R binding peptides were cloned in-frame to the C-terminus of the protein G IgG domain (PG) in a modified pET17b vector (EMD Chemicals, Gibbstown, N.J.) having a ligation independent cloning site (LIC) to generate PG-peptide fusions. The IgG binding domain of protein G is stable and thus enabled easy purification of the fusion protein from bacterial lysates. The amino acid sequence of the protein G IgG domain used is shown in SEQ ID NO: 31. The PG-peptide fusions were expressed in bacteria upon 1 mM IPTG induction and purified using IgG Sepharose beads (GE Healthcare Life Sciences, Piscataway, N.J.) from the bacterial lysates cleared by centrifugation at 16,000 g, 4° C. for 20 min.

Relative binding affinities of the PG-peptide fusions for sIGF1R were measured using ELISA. The Kds were determined using GraphPad Prism 4 software with a one site binding equation. 100 µl of 2 µg/ml sIGF1R(R&D Systems, Minneapolis, Minn.) in Dulbecco's Phosphate Buffer Saline (DPBS (−/−)) was coated onto a 96 well Black Maxisorp plates (Nunc, Rochester, N.Y.) overnight at 4° C. The plates were washed with TBST and the wells blocked with 200 µl/well Starting Block T20 (TBS) (Pierce, Rockford, Ill.) for 1 hr, room temperature with 300 rpm shaking. 75 µl/well of purified, serially diluted PG-peptide fusions, starting concentration 40 µM, was added into the wells and incubated for 1 h, room temperature with 300 rpm mixing; the volume was brought up to 100 µl with Starting Block T20. The plates were washed 3× with TBST and then probed with 100 µl/well Peroxidase labeled-Rabbit antibody (1:5000) (Rockland, Gilbertsville, Pa.), washed, and the signal was detected using 100 µl/well POD substrate (Roche, Indianapolis, Ind.). Chemiluminescence was detected using a Molecular Devices M5 plate reader.

For competition assays, insulin-like growth factor 1 (IGF-1) (R&D Systems, Minneapolis, Minn.) was added to the Starting Block T20 used to bring the volume up to 100 µl at a concentration of 400 nM final.

Characterization of the PG-peptide fusions are summarized in Table 2. The majority of the peptides bound with relative affinities in the low µM range (0.75-8 µM). The fusion protein with peptide clone 17 was unique in its binding profile in that the binding curve was bellshaped. This is similar to insulin binding to the insulin receptor and IGF-1 to the IFG1R, the ligands inducing conformational shifts in the receptors upon binding and having negative cooperativity profiles at higher concentrations of the ligands. The results of the competition studies with IGF-1 are shown in Table 2.

TABLE 2

| Clone number: | Peptide SEQ ID NO: | $EC_{50\,(\mu M)}$ | Competed by IGF-1 | Transcytosis |
|---|---|---|---|---|
| 5 | 1 | 0.75 | — | yes |
| 6 | 2 | 1 | — | yes |
| 7 | 3 | 1.8 | — | not done |
| 8 | 4 | 1.6 | — | yes |
| 9 | 5 | 3.5 | — | no |
| 10 | 6 | 4.3 | — | not done |
| 11 | 7 | 1.2 | yes | no |
| 12 | 8 | 1.8 | — | yes |
| 13 | 9 | >50 | yes | no |
| 14 | 10 | 0.85 | yes | no |
| 15 | 11 | 2.6 | — | not done |
| 16 | 12 | 8.2 | yes | yes |
| 17 | 13 | not done | yes | no |

Example 3

In Vitro BBB Model

Select sIGF1R binding peptides were further characterized in the in vitro blood-brain barrier model, rat brain microvascular endothelial cell model.

Rat Brain capillary endothelial cells were prepared as described (Perriere et al., J. Neurochem. 93:279-289, 2005). Briefly, brains from 6-8 week old male Sprague Dawley rats were rolled on 3 MM chromatography paper to remove the meniges, cut sagitally, and the white matter dissected leaving the cortices, which were then minced thoroughly. The minced cortices were transferred to a 50 ml polypropylene conical tube with 20 ml DMEM supplemented with 39 units/ml DNase I (Worthington, Lakewood, N.J.) and 0.7 mg/ml Collagenase type 2 (Worthington, Lakewood, N.J.) at final concentration and incubated at 37° C. with gentle mixing for 1.25 hrs. After a brief centrifugation the resultant pellet was resuspended in 20 ml 20% BSA (Sigma, St. Louis, Mo.) in DMEM, centrifuged and the microvessel enriched pellet was isolated a digested a second time with 20 ml DMEM supplemented with 39 units/ml DNase 1 and 1 mg/ml Collagenase/Dispase (Roche, Indianapolis, Ind.) at 37° C. for 1 hr. The digestion was briefly centrifuged and the resulting cell pellet was resuspended in 2 ml DMEM and subsequently layered onto the top of a 33% continuous Percoll gradient, centrifuged, and the enriched microvessel fraction was removed and briefly centrifuged a second time. The cell pellet was resuspended in 10 ml complete rat brain microvascular endothelial cell growth media (DMEM, 20% Plasma Derived Serum (PDS), 100 µg/ml Heparin, 2 mM L-Glutamine, 100 U/ml penicillin, 100 µg/ml streptomycin, 0.25 µg/ml amphotericin) and plated onto a 10 cm tissue culture dish for 4 hrs at 37° C., 5% $CO_2$. After 4 hrs cells that remained unattached were pipetted off and counted in a hemacytometer using Trypan Blue. The cells were plated into the top chamber of the Transwells (0.4 µm pore size, diameter 1.12 cm, Corning, Acton, Mass.) treated with 400 µg/ml collagen type IV (Sigma, St. Louis, Mo.) and 100 µg/ml fibronectin (Sigma, St. Louis, Mo.) at a density of $6 \times 10^5$ cells/ml, 500 µl per well. 1 ml of growth media was placed into the bottom chamber. Both chambers were supplemented with 4 µg/ml puromycin (Clontech, Mountain View, Calif.) and the plates were incubated at 37° C., 5% $CO_2$ overnight. The next day the media was changed with fresh complete culture media with 4 µg/ml puromycin and the cells were placed back into the incubator overnight. The next day the media was changed with complete culture media and again two days after. Cultures were monitored by eye till they reached 100% confluence, ~6-7 days after seeding. The developed in vitro BBB model had high transendothelial electrical resistance (>100 ohms-$cm^2$), measured using Millicell-ERS (Millipore, Billercia, Mass.) and very low Na-Fluorescein permeability (about $1-5 \times 10^{-6}$ cm/s).

25 µg of purified peptide-AP fusions were added to the top chamber of the in vitro BBB model and transcytosed peptide-AP fusions were detected at 15 and 30 minute timepoints in the bottom chamber using ELISA. Briefly, 75 µl of each sample was transferred to plates coated with 5 µg/ml mouse monoclonal anti-bacterial AP antibody (Sigma, St. Louis, Mo.). The plate was incubated for 1 hr, washed, the signal was developed with Attophos Substrate (Roche, Indianapolis, Ind.) according to manufacturer's recommendation, and read using a Molecular Devices M5 plate reader with 440 nm excitation and 550 nm emission. The results are shown in Table 2.

The present invention now being fully described, it will be apparent to one of ordinary skill in the art that many changes and modifications can be made thereto without departing from the spirit or scope of the appended claims.

We claim:

1. An isolated polypeptide comprising a polypeptide having a sequence selected from the group consisting of SEQ ID NOs: 1-13.

2. An isolated polynucleotide comprising a polynucleotide encoding a polypeptide having a sequence selected from the group consisting of SEQ ID NOs: 1-13.

3. An isolated polynucleotide comprising a polynucleotide having a sequence selected from the group consisting of SEQ ID NOs: 14-26, or a fully complementary sequence thereof.

4. An isolated vector comprising a polynucleotide having a sequence selected from the group consisting of SEQ ID NOs: 14-26.

5. The vector of claim 4, wherein the vector is an expression vector.

6. An isolated host cell comprising the vector of claim 4.

7. A method of expressing a polypeptide comprising the steps of:
   a. providing the host cell of claim 6; and
   b. culturing the host cell under conditions sufficient for the expression of the polypeptide having a sequence selected from the group consisting of SEQ ID NOs: 1-13.

8. An isolated fusion protein comprising a polypeptide having a sequence selected from the group consisting of SEQ ID NOs: 1-13 fused to a second polypeptide.

9. The fusion protein of claim 8, wherein the second polypeptide encodes an immunoglobulin or fragment thereof.

10. A method for in vitro delivery of a therapeutic agent across endothelial cells, comprising:
    a. conjugating the therapeutic agent to a polypeptide comprising the polypeptide having a sequence selected from the group consisting of SEQ ID NOs: 1, 2, 4, 8, or 12 to form a conjugate;
    b. contacting a polarized monolayer of endothelial cells with the conjugate; and
    c. measuring the amount of the conjugate delivered across the endothelial cells.

11. A method for delivery of a therapeutic agent across the blood-brain barrier, comprising:
    a. conjugating the therapeutic agent to a polypeptide comprising the polypeptide having a sequence selected from the group consisting of SEQ ID NOs: 1, 2, 4, 8, or 12 to form a conjugate; and
    b. administering the conjugate to a mammalian subject.

12. The method of claim 11 wherein the mammalian subject is a human.

* * * * *